(12) United States Patent
Itoh

(10) Patent No.: US 6,743,398 B2
(45) Date of Patent: Jun. 1, 2004

(54) SERUM/CLOT SEPARATION SURFACE DETERMINATION APPARATUS

(76) Inventor: Teruaki Itoh, 5-25, Kokaihommachi, Kumamoto-shi, Kumamoto-ken (JP)

(*) Notice: Subject to any disclaimer, the term of this patent is extended or adjusted under 35 U.S.C. 154(b) by 32 days.

(21) Appl. No.: 10/127,461

(22) Filed: Apr. 23, 2002

(65) Prior Publication Data

US 2002/0155031 A1 Oct. 24, 2002

(30) Foreign Application Priority Data

Apr. 24, 2001 (JP) ........................................ 2001-126379

(51) Int. Cl.[7] ............................................. G01N 33/86
(52) U.S. Cl. ........................ 422/73; 422/82.01; 436/69; 436/149; 436/150
(58) Field of Search ......................... 422/72, 73, 82.01; 436/63, 69, 149, 150; 600/369; 73/64.41

(56) References Cited

U.S. PATENT DOCUMENTS

| | | | |
|---|---|---|---|
| 4,021,340 A | * | 5/1977 | Zine, Jr. .................... 210/789 |
| 4,083,788 A | * | 4/1978 | Ferrara ........................ 210/516 |
| 5,525,298 A | * | 6/1996 | Anami ........................... 422/63 |
| 5,763,265 A | * | 6/1998 | Itsuzaki et al. ............ 435/288.7 |
| 5,980,734 A | * | 11/1999 | Itoh ............................. 210/85 |

FOREIGN PATENT DOCUMENTS

| | | | |
|---|---|---|---|
| JP | 59-637 | * | 1/1984 |
| JP | 03-006523 | * | 1/1991 |
| JP | 6-241862 | * | 9/1994 |
| JP | 7-103970 | * | 4/1995 |
| JP | 8-297043 | * | 11/1996 |
| JP | 9-133687 | * | 5/1997 |
| JP | 9-304398 | * | 11/1997 |
| JP | 10-272595 | * | 10/1998 |
| JP | 11-14433 | * | 1/1999 |
| JP | 2001-108506 | * | 4/2001 |

* cited by examiner

Primary Examiner—Maureen M. Wallenhorst
(74) Attorney, Agent, or Firm—Nixon & Vanderhye, PC

(57) ABSTRACT

A serum/clot separation surface determination apparatus includes a test tube formed of a non-magnetic material containing a blood sample which is separated into a serum and a clot by a silicon separating medium, a detection coil fitted on an outer surface of the test tube, a measurement signal supply unit which supplies a measurement signal having a given frequency to the detection coil, a drive control unit which variably controls a relative position between the detection coil and the test tube in a longitudinal direction of the test tube by moving at least one of the detection coil and the test tube, a signal level detector which detects a level of the measurement signal that varies with the relative position, and a determination unit which determines a position of a sample separation surface obtained by the silicon separating medium, based on the level of the detected measurement signal.

18 Claims, 2 Drawing Sheets

SERUM/CLOT SEPARATION SURFACE DETERMINATION APPARATUS

CROSS-REFERENCE TO RELATED APPLICATIONS

This application is based upon and claims the benefit of priority from the prior Japanese Patent Application No. 2001-126379, filed Apr. 24, 2001, the entire contents of which are incorporated herein by reference.

BACKGROUND OF THE INVENTION

1. Field of the Invention

The present invention relates to a serum/clot separation surface determination apparatus for automatically determining a position of the separation surface (serum-side or clot-side separation surface) of a blood sample that is contained in a test tube and separated into a serum and clot up and down by a silicon-separating medium.

2. Description of the Related Art

In order to accurately separate blood into a serum and a clot using a centrifuge or the like, a separating medium such as a silicon-separating medium is put into a test tube. Using such a test tube including a separating medium, a blood sample containing a serum and a clot that are separated up and down by a silicon separating medium is obtained in the test tube after centrifugal separation.

When the blood sample so obtained undergoes the following processing, it is required that a separation surface of the blood sample, especially a position of the serum-side separation surface be accurately determined. Conventionally, the determination has been performed chiefly by a visual check and using an optical sensor.

In the visual check, it takes time to confirm the position of a separating medium and the separation surface is likely to be determined inaccurately; therefore, there were many cases where an operator could not correctly know an amount of serum included in a test tube. There was a problem that the post-processing was very complicated and a lot of time and trouble was required. On the other hand, the optical sensor complicates the structure of the apparatus since a light-shield means needs to be provided to prevent extraneous light from entering.

BRIEF SUMMARY OF THE INVENTION

An object of the present invention is to provide a serum/clot separation surface determination apparatus having the following advantages.

(a) The serum-side or clot-side separation surface can be determined speedily and accurately and the post-processing can be very simplified.

(b) The apparatus is simple in structure and easy to manufacture.

In order to attain the above object, the serum/clot separation surface determination apparatus according to the present invention has the following characteristic structures. The other characteristic structures will be clarified in the Detailed Description of the Invention.

A serum/clot separation surface determination apparatus according to an aspect of the present invention comprises a test tube containing a blood sample which is separated into a serum and a clot by a silicon separating medium, a test tube holder which holds the test tube, a detection coil fitted on an outer surface of the test tube held by the test tube holder, a measurement signal supply unit which supplies a measurement signal having a given frequency to the detection coil, position control means which variably controls a relative position between the detection coil and the test tube in a longitudinal direction of the test tube by moving at least one of the detection coil and the test tube, signal level detection means which detects a level of the measurement signal that varies with the relative position controlled by the position means, and determination means which determines a position of a sample separation surface obtained by the silicon separating medium, based on the level of the measurement signal detected by the signal level detection means.

The above serum/clot separation surface determination apparatus has the following advantages. The relative permeability of the silicon-separating medium that separates the blood sample into the serum and clot clearly differs from that of the serum or clot. As the drive control unit varies a relative position between the detection coil and test tube, the level of a measurement signal having a given frequency supplied to the detection coil suddenly changes in a position of the silicon separating medium. The signal level detection means automatically detects a point at which the level of the measurement signal increases or decreases suddenly. It is thus possible to accurately determine a position of the sample separation surface.

Consequently, a position of the separation surface between the serum and clot can be determined speedily and accurately, and the subsequent process can be very simplified.

Since the detection coil is used as a sensor, a light-shield means for preventing extraneous light from entering as noise components need not be provided, as compared with an apparatus using an optical sensor or the like. Therefore, the apparatus of the present invention is simple in structure and easy to manufacture.

DETAILED DESCRIPTION OF THE INVENTION

Embodiment

[Structure]

Figure 1:
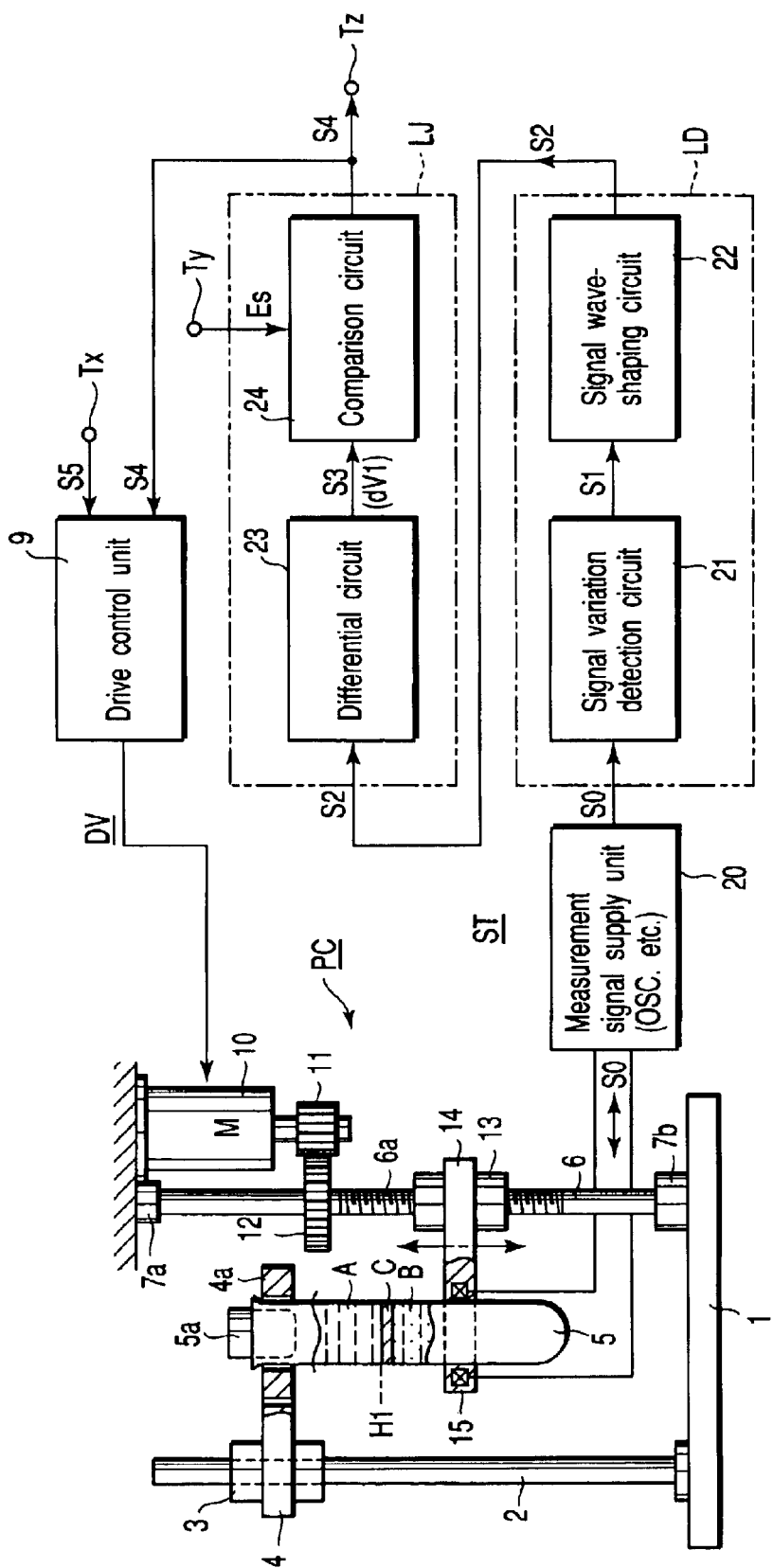
FIG. 1 is a block diagram showing a structure of a serum/clot separation surface determination apparatus according to an embodiment of the present invention.

In FIG. 1, reference numeral 1 indicates a mounting base plate. A strut 2 is implanted into the mounting base plate 1. The proximal end portion of a test tube holder 4 is attached to an upper portion of the strut 2 through a supporting member 3 that is capable of moving the holder 4 up and down. The holder 4 includes a test tube holding section 4a (having a test tube supporting hole or a test tube chuck mechanism) at the distal end portion (right end portion in the figure) thereof. A test tube 5 is formed of non-magnetic material such as glass of resin. The test tube holder 4 holds the test tube 5 in such a position that the longitudinal direction of the test tube 5 is substantially equal to a vertical line. The test tube 5 contains a sample that has been centrifugalized or a blood sample that is separated into a serum A and a clot B by a silicon-separating medium C. The opening of the test tube 5 is hermetically sealed with a stopper 5a.

A screw shaft 6 is rotatably supported by bearings 7a and 7b at a given distance from the strut 2. The screw shaft 6 is rotated forward or backward by a drive system DV. The drive system DV includes a drive control unit 9 that operates in response to an external operation signal S5 supplied from a terminal Tx (described later) and a signal S4 fed back from a signal processing system ST, a drive motor 10 using a step motor, a servo motor or the like, which is rotated forward and backward by the drive control unit 9, and reduction gear mechanisms 11 and 12 for decelerating the drive motor 10 and transmitting its rotation.

A movable nut 13 having a screw section on its inner surface is screwed on a screw section 6a of the screw shaft 6. The movable nut 13 moves up and down, as indicated by a double-headed arrow, in accordance with the rotation of the screw shaft 6. The proximal end portion of a coil supporter 14 is supported on the movable nut 13. A detection coil 15 is attached to the distal end portion (left end portion in the figure) of the coil supporter 14.

The detection coil 15 is a toroidal one having conductors wound on a reel. The test tube 5 is fitted into a hollow of the detection coil 15 with a slight clearance between the hollow and the outer surface of the test tube 5.

If the drive motor 10 rotates the screw shaft 6 forward or backward, the detection coil 15 moves up and down. Consequently, a relative position between the detection coil 15 and the test tube 5 in its longitudinal direction can variably be controlled. The screw shaft 6, drive control unit 9, drive motor 10, reduction gear mechanisms 11 and 12, movable nut 13, and coil supporter 14 compose a position control means PC of the present invention.

A measurement signal supply unit 20 includes a variable frequency oscillator and can send out an oscillation output having a varied frequency as a measurement signal S0. The measurement signal S0 is supplied to the detection coil 15 and a signal variation detection circuit 21. The circuit 21 detects a level variation of the measurement signal (oscillation output) S0 and supplies it to a signal wave-shaping circuit 22 as a detection signal S1. An alternating field is generated from the detection coil 15 and acts on the blood sample TS contained in the test tube 5, with the result that the level variation of the measurement signal (oscillation output) S0 is caused on the basis of impedance variations that occur in accordance with the relative permeability of the blood sample TS.

The signal wave-shaping circuit 22 rectifies and smoothens an input detection signal S1 and shapes its waveform. Then, the circuit 22 supplies it to a differential circuit 23 as a level signal S2. The above circuits 21 and 22 compose a signal level detection means LD of the present invention.

The differential circuit 23 differentiates the level signal S2 to generate a differential signal S3 including a falling differential signal dv0 and a rising differential signal dv1. In the present embodiment, only the rising differential signal dv1 of the differential signal S3 is supplied to a comparison circuit 24. The comparison circuit 24 compares the rising differential signal dv1 with a reference signal Es that is to be supplied to a terminal Ty. When the rising differential signal dv1 exceeds the reference signal Es, the comparison circuit 24 outputs a serum-side separation surface determination signal 54. The signal S4 is output from an output terminal Tz and fed back to the drive control unit 9 as a return operation command signal. The differential circuit 23 and comparison circuit 24 compose a determination means LJ of the present invention.

[Operation]

The above-described serum/clot separation surface determination apparatus according to the embodiment of the present invention operates as follows. Assume that a first sample-contained test tube 5 is conveyed to the determination apparatus by a conveyance mechanism (a belt conveyor, etc.), which is not shown. Then, the test tube 5 is moved to the test tube holder 4 by a robot arm not shown. Concurrently with this, an external operation signal S5 is supplied to the drive control unit 9 from the terminal Tx and thus the unit 9 starts to operate. The drive motor 10 first rotates in the forward direction and the screw shaft 6 rotates forward. As a result, the detection coil 15 goes up at a constant speed.

Figure 2:
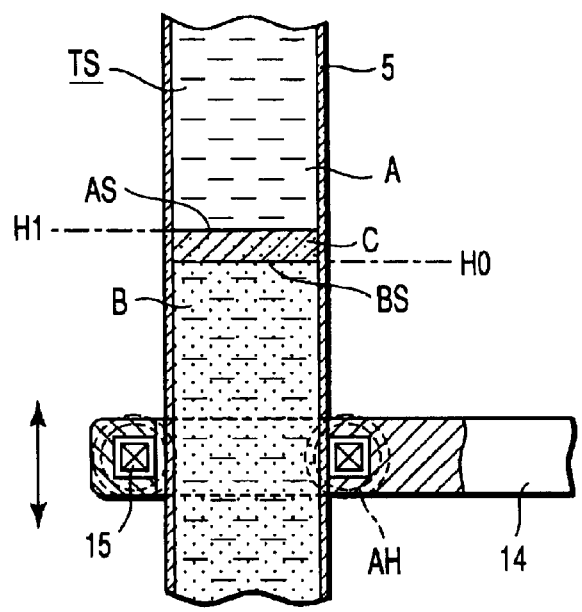
FIG. 2 is a sectional view explaining an operation of the serum/clot separation surface determination apparatus according to the embodiment of the present invention and showing a position of a detection coil relative to a test tube.

Then, the measurement signal supply unit 20 supplies a measurement signal S0 having a given frequency to the detection coil 15. As illustrated in FIG. 2, therefore, an alternating field AH generated from the detection coil 15 links with a blood sample TS. Consequently, the measurement signal S0 varies in level in accordance with the relative permeability of the blood sample TS contained in the test tube 5. The signal variation detection circuit 21 of the signal level detection means LD detects a level variation of the measurement signal S0 and transmits it to the signal wave-shaping circuit 22 as a detection signal S1.

Figure 3:
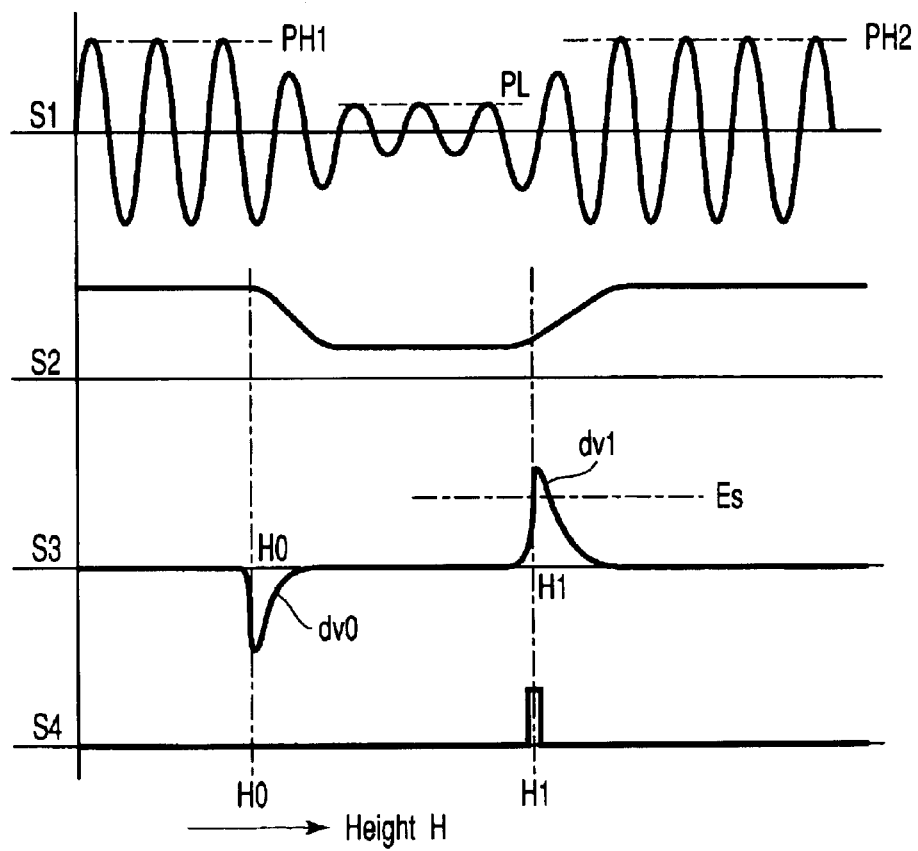
FIG. 3 is a waveform chart explaining an operation of the serum/clot separation surface determination apparatus according to the embodiment of the present invention and showing a model of signal variations of respective components of a measurement system with the height of the detection coil.

At the first stage, the alternating field AH links with a clot B. Since the relative permeability of the clot B including a large number of red blood cells is relatively high, the level of the detection signal S1 has a relatively large peak value PH1 as shown in FIG. 3. When the linkage position of the alternating field AH coincides with the position of a silicon separating medium C in a boundary between the clot B and serum A, the level of the detection signal 31 lowers from PH1 to PL as shown in FIG. 3 since the relative permeability of the silicon separating medium C is smaller than that of the clot B. When the linkage position of the alternating field AH coincides with the position of the serum A, the peak value of the detection signal S1 rises from PL to PH2 since the relative permeability of the serum A is relatively lager than that of the silicon separating medium C.

In other words, since the relative permeability of the silicon separating medium C is considerably smaller than that of the serum A and that of the clot B, the level of the detection signal S1 does not vary greatly at heights of H0 and H1 of the upper and lower separation surfaces of the silicon separating medium C.

The detection signal S1 whose level varies as described above is rectified and smoothed by the signal wave-shaping circuit 22 and input to the differential circuit 23 of the determination means LJ as a level signal S2 as illustrated in FIG. 3. The differential circuit 23 differentiates the rise and fall of the input level signal S2. In the differentiated signal S3, a rising differential signal dv1 obtained at a height of H1 is supplied to the comparison circuit 24. The comparison circuit 24 compares the level of the differential signal dv1 with that of a reference signal Es to be supplied to the terminal Ty. When the level of the differential signal dv1 exceeds that of the reference signal Es, the comparison circuit 24 sends out a determination signal S4 that indicates a serum-side separation surface AS of the silicon separating medium C. The determination signal is output from the output terminal Tz and fed back to the drive control unit 9 as a return operation command signal. The drive control unit 9 stops an ascent control operation of the detection coil 15 and then starts a descent control operation. The detection coil 15 descends to the initial position. When the descent operation is completed, the determination signal S4 is shut off.

At roughly the same time, the test tube 5 is removed from the test tube holder 4 by the robot arm not shown and returned to the conveyance mechanism. The determination result of the serum-side separation surface AS in the first test tube 5 is stored as determination result data in a memory such as a CPU not shown, and the data is recorded on a barcode label (not shown) or the like, which is placed in the middle of the test tube 5.

When the conveyance mechanism conveys a second sample-contained test tube 5 to the determination apparatus, the apparatus performs a separation surface determination operation for the second test tube 5, as for the first test tube. After that, the same operations are repeated and the determination operation is completed.

Features of the Embodiments

[1] A serum/clot separation surface determination apparatus according to the embodiment of the present invention comprises a test tube 5 formed of non-magnetic material containing a blood sample TS which is separated into a serum A and a clot B by a silicon separating medium C, a test tube holder 4 which holds the test tube 5, a detection coil 15 fitted on an outer surface of the test tube 5 held by the test tube holder 4, a measurement signal supply unit (including a variable frequency oscillator) 20 which supplies a measurement signal S0 having a given frequency to the detection coil 15, position control means PC which variably controls a relative position between the detection coil 15 and the test tube 5 in a longitudinal direction of the test tube by moving (up and down) at least one of the detection coil 15 and the test tube 5, signal level detection means LD (including a signal variation detection circuit 21 and a signal wave-shaping circuit 22) which detects a level of the measurement signal S0 that varies with the relative position controlled by the position control means PC, and determination means LJ (including a differential circuit 23 and a comparison circuit 24) which determines a position (at least height H1 of serum-side separation surface AS in the test tube 5) of a sample separation surface (at least serum-side separation n surface AS) obtained by the silicon separating medium C, based on the level of the measurement signal S0 detected by the signal level detection means LD.

The above serum/clot separation surface determination apparatus has the following advantages. The relative permeability of the silicon-separating medium C that separates the blood sample into the serum A and clot B clearly differs from that of the serum A or clot B. As the drive control unit 9 varies a relative position between the detection coil 15 and test tube 5, the level of a measurement signal S0 having a given frequency supplied to the detection coil 15 suddenly changes in a position of the silicon separating medium C. The signal level detection means LD automatically detects a point at which the level of the measurement signal S0 increases or decreases suddenly. It is thus possible to accurately determine a position (a position of serum-side separation surface AS in this embodiment) of the sample separation surface.

[2] In the serum/clot separation surface determination apparatus described in the above paragraph [1], the measurement signal supply unit 20 includes a variable frequency oscillator which sends out an oscillation output having a varied frequency.

[3] In the serum/clot separation surface determination apparatus described in the above paragraph [1] or [2], the signal level detection means LD includes a signal variation detection circuit 21 and a signal wave-shaping circuit 22.

[4] In the serum/clot separation surface determination apparatus described in the above paragraph [1] or [2], the determination means LJ includes a differential circuit 23 and a comparison circuit 24.

[5] In the serum/clot separation surface determination apparatus described in the above paragraph [1] or [2], the signal level detection means LD includes a signal variation detection circuit 21 and a signal wave-shaping circuit 22, and the determination means LJ includes a differential circuit 23 and a comparison circuit 24.

Modifications

The serum/clot separation surface determination apparatus according to the embodiment can be modified as follows:

i) If the test tube 5 is moved up and down, a relative position between the test tube 5 and the detection coil 15 can variably be controlled.

ii) If a plurality of test tubes held together and a plurality of detection coils attached and opposed to the test tubes are moved relative to each other at roughly the same time and each of the detection coils is supplied with a measurement signal having a given frequency, the separation surfaces of the blood samples contained in the respective test tubes can be determined almost at roughly the same time.

What is claimed is:

1. A serum/clot separation surface determination apparatus comprising:

a test tube containing a blood sample which is separated into a serum and a clot by a silicon separating medium having a permeability smaller than that of the serum/clot;

a test tube holder which holds the test tube;

a detection coil fitted on an outer surface of the test tube held by the test tube holder;

a measurement signal supply unit which supplies a measurement signal having a given frequency to the detection coil;

position control means which starts operation in response to a control signal for variably controlling a relative position between the detection coil and the test tube in a longitudinal direction of the test tube by moving at least one of the detection coil and the test tube and for performing a return operation to return the detection coil and the test tube to an initial position in response to a return operation signal;

signal level detection means which detects a level of the measurement signal that varies with the relative position controlled by the position control means; and determination means which determines a position of a sample separation surface obtained by the silicon separating medium based on the level of the measurement signal detected by the signal level detection means, wherein the determination means comprises means for differentiating a rising of the measurement signal corresponding to a surface of the separating medium to form a differential signal, means for outputting a serum separation surface judgment signal when a level of the differential signal exceeds a level of a reference signal, and means for providing the judgment signal to the position control means as the return operation signal, when the detection coil moves upward and the test tube moves downward relative to each other.

2. The serum/clot separation surface determination apparatus according to claim 1, wherein the measurement signal supply unit includes a variable frequency oscillator which sends out an oscillation output having a varied frequency.

3. The serum/clot separation surface determination apparatus according to claim 2, wherein the signal level detection means includes a signal variation detection circuit and a signal wave-shaping circuit.

4. The serum/clot separation surface determination apparatus according to claim 2, wherein the determination means includes a differential circuit and a comparison circuit.

5. The serum/clot separation surface determination apparatus according to claim 2, wherein the signal level detection means includes a signal variation detection circuit and a signal wave-shaping circuit, and the determination means includes a differential circuit and a comparison circuit.

6. The serum/clot separation surface determination apparatus according to claim 1, wherein the signal level detection means includes a signal variation detection circuit and a signal wave-shaping circuit.

7. The serum/clot separation surface determination apparatus according to claim 1, wherein the determination means includes a differential circuit and a comparison circuit.

8. The serum/clot separation surface determination apparatus according to claim 1, wherein the signal level detection means includes a signal variation detection circuit and a signal wave-shaping circuit, and the determination means includes a differential circuit and a comparison circuit.

9. A separating medium surface detecting apparatus for detecting a surface of a separating medium for separating serum and a clot of a blood sample contained in a test tube, the separating medium surface detecting apparatus comprising:
   a detecting coil supplied with a measurement signal, wherein the detecting coil is disposed adjacent to an outer surface of the test tube;
   a drive unit for providing relative movement of the detecting coil and the test tube from an initial relative position;
   level detection circuitry for detecting a level of the measurement signal as the detecting coil and the test tube move relative to each other; and
   a surface determination unit for differentiating the level of the measurement signal, outputting a separating medium surface signal indicative of a surface of the separating medium when the differentiated level has a predetermined relationship to a reference signal, and supplying the separating medium surface signal to the drive unit as a signal to return the coil and the test tube to the initial relative position.

10. The separating medium surface detecting apparatus according to claim 9, wherein the separating medium comprises a silicon separating medium.

11. The separating medium surface detecting apparatus according to claim 9, wherein a relative permeability of the separating medium is smaller than relative permeabilities of the serum and the clot.

12. The separating medium surface detecting apparatus according to claim 9, wherein the separating medium surface signal is output when the differentiated level exceeds a level of the reference signal.

13. The separating medium surface detecting apparatus according to claim 9, wherein the separating medium surface signal is indicative of a serum-side surface of the separating medium.

14. The separating medium surface detecting apparatus according to claim 9, wherein the separating medium surface signal is indicative of a clot-side surface of the separating medium.

15. A separating medium surface detecting apparatus for detecting a surface of a separating medium for separating serum and a clot of a blood sample contained in a test tube, the separating medium surface detecting apparatus comprising:
   a detecting coil supplied with a measurement signal, wherein the detecting coil is disposed adjacent to an outer surface of the test tube;
   a drive unit for providing relative movement of the detecting coil and the test tube from an initial relative position;
   level detection circuitry for detecting a level of the measurement signal as the detecting coil and the test tube move relative to each other; and
   a surface determination unit for detecting sudden changes in the detected level of the measurement signal due to permeability differences among the serum, the clot and the separating medium and, if the sudden changes have a predetermined relationship to a reference signal, generating a separating medium surface detection signal indicative of a surface of the separating medium and supplying this generated signal to the drive unit as a signal to return the detecting coil and the test tube to the initial relative position.

16. The separating medium surface detecting apparatus according to claim 15, wherein the separating medium surface detection signal is indicative of a serum-side surface of the separating medium.

17. The separating medium surface detecting apparatus according to claim 15, wherein the separating medium surface detection signal is indicative of a clot-side surface of the separating medium.

18. A separating medium surface detecting apparatus for detecting a surface of a separating medium for separating serum and a clot of a blood sample contained in a test tube, the separating medium surface detecting apparatus comprising:
   a detector supplied with a measurement signal, wherein the detector is disposed adjacent to an outer surface of the test tube;
   drive means for providing relative movement of the detector and the test tube from an initial relative position;
   level detection means for detecting a level of the measurement signal as the detector and the test tube move relative to each other; and
   a surface determination means for detecting sudden changes in the detected level of the measurement signal due to permeability differences among the serum, the clot and the separating medium and, if the sudden changes have a predetermined relationship to a reference signal, generating a separating medium surface detection signal indicative of a surface of the separating medium and supplying this generated signal to the drive means as a signal to return the detector and the test tube to the initial relative position.

* * * * *

UNITED STATES PATENT AND TRADEMARK OFFICE
CERTIFICATE OF CORRECTION

PATENT NO. : 6,743,398 B2
DATED : June 1, 2004
INVENTOR(S) : Itoh

It is certified that error appears in the above-identified patent and that said Letters Patent is hereby corrected as shown below:

<u>Title page,</u>
Item [56], References Cited, FOREIGN PATENT DOCUMENTS, please add
-- JP 05-040447 10/1993 --.

Signed and Sealed this

Seventh Day of December, 2004

JON W. DUDAS
*Director of the United States Patent and Trademark Office*